(12) United States Patent
Tsuyutani et al.

(10) Patent No.: US 6,710,199 B2
(45) Date of Patent: Mar. 23, 2004

(54) PROCESS FOR PREPARING PHOSPHORIC ESTER

(75) Inventors: Shinji Tsuyutani, Wakayama (JP); Kengo Shibata, Wakayama (JP); Kazunori Aizawa, Tokyo (JP); Masaru Sakata, Wakayama (JP); Mitsugu Morishita, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/157,495

(22) Filed: May 30, 2002

(65) Prior Publication Data

US 2003/0065205 A1 Apr. 3, 2003

(30) Foreign Application Priority Data

| May 31, 2001 | (JP) | ................................ | 2001-165040 |
| May 31, 2001 | (JP) | ................................ | 2001-165056 |
| Sep. 25, 2001 | (JP) | ................................ | 2001-291848 |
| Nov. 20, 2001 | (JP) | ................................ | 2001-355203 |
| Nov. 21, 2001 | (JP) | ................................ | 2001-355728 |

(51) Int. Cl.$^7$ ................................. C07F 9/09
(52) U.S. Cl. ..................................... 558/114
(58) Field of Search ......................... 558/114

(56) References Cited

U.S. PATENT DOCUMENTS 5,883,280 A * 3/1999 Tsuyutani et al.
6,034,261 A * 3/2000 Matsunaga et al.
6,407,277 B1 * 6/2002 Matsunaga et al.

FOREIGN PATENT DOCUMENTS

| GB | 1160951 | 8/1969 |
| JP | 56 079697 | 6/1981 |
| JP | 11 255785 | 9/1999 |
| JP | 2001 226386 | 8/2001 |

* cited by examiner

Primary Examiner—Joseph K. McKane
Assistant Examiner—Golam M M Shameem
(74) Attorney, Agent, or Firm—Oblon, Spivak, McClelland, Maier & Neustadt, P.C.

(57) ABSTRACT

A process for preparing a phosphoric ester having reduced odor, comprising contacting a phosphoric ester with at least one of an inert gas and steam at 100° to 160° C. in a packed tower; a process for preparing a phosphoric ester having reduced odor, comprising repeating a set of processes comprising (A) heating a phosphoric ester, and contacting the heated phosphoric ester with at least one of an inert gas and steam; and (B) cooling the phosphoric ester obtained in the step (A); a process for preparing a phosphoric ester having reduced odor, comprising adding water to a phosphoric ester, and distilling water from the phosphoric ester under reduced pressure; and a process for preparing a phosphoric ester having reduced odor, comprising reacting an organic hydroxy compound with a phosphorylation agent, while introducing an inert gas into the mixture of the organic hydroxy compound and the phosphorylation agent. The phosphoric ester is useful for, for instance, a shampoo, a cleaning agent, a facial cleansing agent, an emulsifier, and the like.

14 Claims, 1 Drawing Sheet

PROCESS FOR PREPARING PHOSPHORIC ESTER

BACKGROUND OF THE INVENTION

1. Field of the Invention

The present invention relates to a process for preparing a phosphoric ester. More specifically, the present invention relates to a process for preparing a phosphoric ester which is useful for, for instance, a shampoo, a cleaning agent, a facial cleansing agent, an emulsifier, and the like.

2. Discussion of the Related Art

A phosphoric ester of an organic hydroxy compound (hereinafter also referred to as "phosphoric ester") has been used in the field of a cleaning agent, an emulsifier, a fiber-treating agent, an anticorrosive agent, pharmaceuticals and the like. Especially, an alkali metal salt such as a potassium or sodium salt of a monoalkyl phosphoric ester having a long-chain alkyl group, and an alkanolamine salt such as triethanolamine are useful for articles which are directly used for human bodies, such as a shampoo and a facial cleansing agent, because they have water solubility, are excellent in foaming power and detergency, and exhibit low toxicity and low skin irritability. When the phosphoric ester is contained in the articles which are directly used for human bodies, weak odor is required for the phosphoric ester in its quality.

The phosphoric ester has been prepared by reacting an organic hydroxy compound with a phosphorylation agent such as phosphorus pentoxide, polyphosphoric acid or phosphorus oxychloride. However, there exist as impurities in the phosphoric ester an unreacted organic hydroxy compound and a by-product such as an olefine generated during the phosphorylation reaction. These impurities may give wrong influence to the phosphoric ester because the impurities act as odorous components, so that a complicated process for removing the odorous components would be necessitated after the reaction.

As a deodorization process for removing impurities such as an organic hydroxy compound, there have been proposed a process comprising re-crystallizing with a solvent to remove impurities from the phosphoric ester as disclosed in Japanese Patent Laid-Open No. Hei 11-158193, and an extraction process comprising reacting a phosphoric ester with a basic compound to give a salt of the phosphoric ester, and extracting odorous components to an organic layer and the salt of the phosphoric ester to an aqueous layer with a solvent as disclosed in Japanese Examined Patent Publication No. Hei 03-027558.

However, according to these processes, since the solvent is used in a large amount, there is necessitated an equipment for collecting the solvent. In addition, according to the process comprising recrystallizing the phosphoric esters to remove impurities, when the phosphoric ester is a phosphoric ester having a distribution in an alkyl moiety or a phosphoric ester having a distribution in the number of moles added of the alkylene oxide adduct is used, the distribution states of the alkyl moiety or the alkylene oxide adduct of the phosphoric ester after the treatment would change from that before the treatment, so that a problem would be caused in the preparation of a product, and moreover the loss of a solvent used for the phosphoric ester is unavoidable. Also, according to the extraction process, a complicated process for collecting a solvent is necessitated because this process requires a lower alcohol as a demulsifier besides the extraction solvent, and as a result, investment costs for its equipments would be increased.

As described above, there are some defects in the processes using a solvent such that the productivity is lowered, and investment costs for equipments are increased, so that necessary costs become higher.

On the other hand, as a deodorization process using no solvent, there have been proposed a process comprising contacting a phosphoric ester with an inert gas including steam with a rotary thin-film-type evaporator, or a thin-film deodorizing tower such as a wet wall tower as disclosed in Japanese Examined Patent Publication No. Sho 62-025155, and a process comprising carrying out phosphorylation reaction with blowing steam into raw materials as disclosed in Japanese Examined Patent Publication No. Hei 05-066958.

However, when odorous components are removed by blowing an inert gas with a rotary thin-film-type evaporator, or a thin-film deodorizing tower such as a wet wall tower, since the contact area between the vapor phase and the liquid phase is smaller as compared to the size of the whole apparatus, the contact efficiency is lower, a larger amount of the inert gas is required, and the apparatus becomes larger, so that the investment costs for the equipment become larger, thereby increasing the cost. In addition, since the amount of waste water or the amount of exhaust gas is increased, the treatment costs would be increased.

In addition, when steam is blown into the raw materials during the phosphorylation reaction, phosphorus pentoxide or polyphosphoric acid which is a phosphorylation agent having a pyrophosphate bond would be decomposed by steam, thereby inhibiting the reaction with the organic hydroxy compound. Therefore, the amount of an unreacted organic hydroxy compound increases, and a wrong influence is given to odor.

Therefore, it has been earnestly desired to develop an industrial process for economically and advantageously preparing a phosphoric ester having reduced odor, capable of easily reducing odorous components remaining in the phosphoric ester.

An object of the present invention is to provide a process capable of easily and rapidly preparing a phosphoric ester having reduced odor.

These and other objects of the present invention will be apparent from the following description.

SUMMARY OF THE INVENTION

According to the present invention, there are provided:

(1) a process for preparing a phosphoric ester having reduced odor, comprising contacting a phosphoric ester with at least one of an inert gas and steam at 100° to 160° C. in a packed tower;

(2) a process for preparing a phosphoric ester having reduced odor, comprising repeating a set of processes comprising:
  (A) heating a phosphoric ester, and contacting the heated phosphoric ester with at least one of an inert gas and steam; and
  (B) cooling the phosphoric ester obtained in the step (A);

(3) a process for preparing a phosphoric ester having reduced odor, comprising adding water to a phosphoric ester, and distilling water from the phosphoric ester under reduced pressure; and (4) a process for preparing a phosphoric ester having reduced odor, comprising reacting an organic hydroxy compound with a phosphorylation agent, while introducing an inert gas into the mixture of the organic hydroxy compound and the phosphorylation agent.

DETAILED DESCRIPTION OF THE INVENTION

Figure 1:
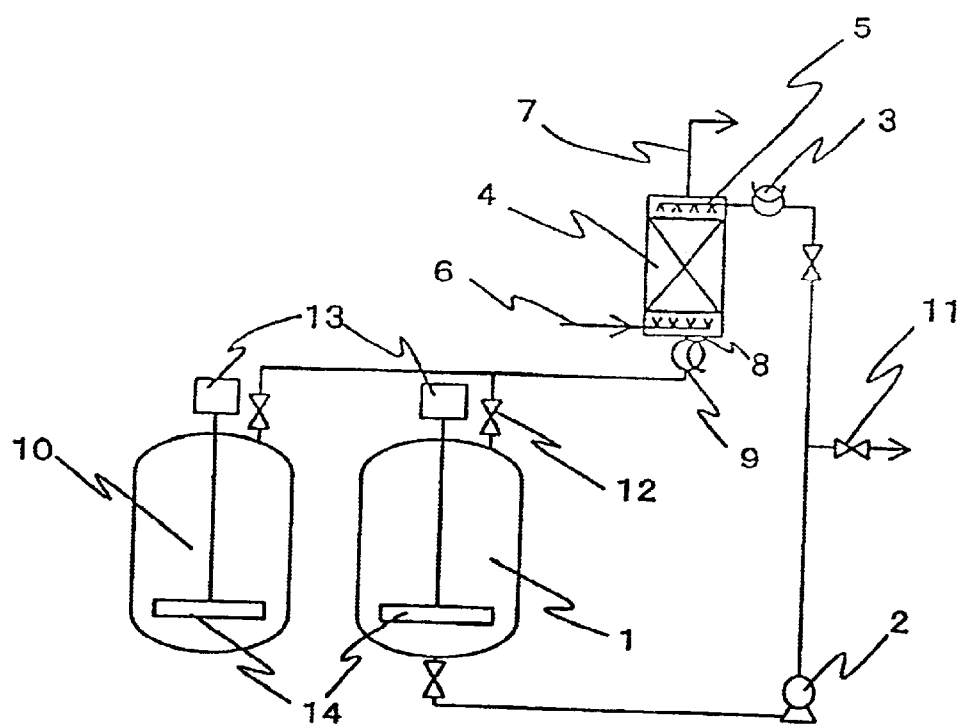
FIG. 1 is a schematic explanatory view for a process for preparing a phosphoric ester of the present invention.

The phosphoric ester used in the present invention is a phosphoric ester of an organic hydroxy compound, and includes those prepared by the reaction of an organic hydroxy compound with at least one phosphorylation agent selected from phosphorus pentoxide, polyphosphoric acid, orthophosphoric acid and phosphorus oxychloride. Among them, a phosphoric ester prepared by the reaction of at least one phosphorylation agent selected from the group consisting of orthophosphoric acid, polyphosphoric acid and phosphorus pentoxide with the organic hydroxy compound is preferable, because by-products such as hydrochloric acid gas are not generated, so that a specialized equipment therefor is not required.

When phosphorus pentoxide and polyphosphoric acid are used as the phosphorylation agent, it is preferable that the amount of water is usually 0.5 to 1.5 mol, and that the amount of the organic hydroxy compound is usually 1 to 3 mol, per one mol of phosphorus pentoxide which corresponds to 138% by weight of the amount of orthophosphoric acid and the value obtained by dividing the concentration of polyphosphoric acid by 138 (hereinafter referred to the same), from the viewpoint of reducing the generation of a by-product, i.e. orthophosphoric acid which causes wrong influences to the stability of a manufactured article such as a cleaning agent prepared by using the phosphoric ester as a raw material, and from the viewpoint of the reduction of a by-product, i.e. phosphoric diester which causes wrong influences to detergency.

It is preferable that the above-mentioned phosphorylation reaction is carried out under conditions such that the value of the formula (1):

[(Number of moles of organic hydroxy compound added)+(Number of moles of water including the number of moles of nH$_2$O contained in the phosphorylation agent represented by P$_2$O$_5$.nH$_2$O)]÷(Number of moles of the phosphorylation agent when the amount of the phosphorylation agent is converted to the amount of P$_2$O$_5$) (1)

is 2.8 to 3.1. When the value of the formula (1) is 3.0, the amounts of the phosphorylation agent, the organic hydroxy compound and water are controlled to the above-mentioned stoichiometric amounts. When the value of the formula (1) is controlled to the above-mentioned range, there are some advantages such that the amount of unreacted residual organic hydroxy compound is reduced, and that the decomposition of the generated phosphoric ester is suppressed during the reaction. The value of the formula (1) is more preferably 2.9 to 3.0.

The phosphoric ester usually contains the unreacted organic hydroxy compound, a compound derived from the organic hydroxy compound and by-products generated during the phosphorylation reaction as odorous components.

When a pyrophosphate bond remains in the phosphoric ester, water can be added to the phosphoric ester to hydrolyze the pyrophosphate, from the viewpoint of the improvement in stability when the phosphoric ester is used in a manufactured article. The amount of water added for hydrolysis is not limited to specified ones. The amount of water added is adjusted so that the water content in the phosphoric ester during the hydrolysis is preferably at most 10% by weight, more preferably at most 5 by weight, still more preferably at most 3% by weight, from the viewpoints of the avoidance of gelation, corrosion of equipments and foaming in the subsequent deodorizing treatment. In addition, the water content in the phosphoric ester during the hydrolysis is preferably at least 0.01% by weight, more preferably at least 0.1% by weight, from the viewpoint of efficiently carrying out the hydrolysis. From these viewpoints, the water content is preferably 0.01 to 10% by weight, more preferably 0.1 to 5% by weight, still more preferably 0.1 to 3% by weight.

The conditions for the hydrolysis are not limited to specified ones. It is preferable that hydrolysis is carried out, for instance, at 60° to 120° C. for 0.1 to 10 hours or so.

After the hydrolysis, the dehydration can be carried out so that the water content in the phosphoric ester becomes at most 3% by weight, from the viewpoints of the avoidance of corrosion of equipments and foaming in the subsequent deodorizing treatment.

The organic hydroxy compound is an organic compound having a hydroxyl group. Examples of the organic hydroxy compound include linear or branched, saturated or unsaturated alcohols, alkylene oxide adducts of these alcohols (number of carbon atoms of alkylene oxide being 2 to 4) and the like. These organic hydroxy compounds can be used alone or in admixture of at least two kinds. Among them, there are preferable an alcohol having 6 to 30 carbon atoms and a polyoxyalkylene alkyl ether prepared by adding an alkylene oxide having 2 to 4 carbon atoms to this alcohol in an average number of moles added of 1 to 10 mol. There are more preferable an alcohol having 8 to 14 carbon atoms, and a polyoxyalkylene alkyl ether prepared by adding an alkylene oxide having 2 to 4 carbon atoms to this alcohol in an average number of moles added of 2 to 5 mol, and preferably 2 to 4 mol. Representative examples of the organic hydroxy compound include undecyl alcohol and its ethylene oxide adduct in which the number of moles ethylene oxide added is 3, dodecyl alcohol and its ethylene oxide adduct in which the number of moles of ethylene oxide added is 2, and the like.

The "inert gas" as referred to herein means a gas which would not impart wrong influences to the quality and yield of the phosphoric ester under the treatment conditions for reducing the odorous components. The inert gas includes nitrogen gas, argon gas, helium gas, carbon dioxide gas, and the like. Among them, nitrogen gas and carbon dioxide gas are preferable, and nitrogen gas is more preferable.

Among the inert gas and steam, steam is preferable, because the steam can be easily condensed, so that the load of the thermal energy for the condenser can be reduced, and the load for the exhaust can be also reduced.

The ratio of the flow rate of at least one of the inert gas and steam to the flow rate of the phosphoric ester [flow rate of at least one of the inert gas and steam (m$^3$/h)/flow rate of the phosphoric ester (kg/h)] is preferably 0.1 to 3, more preferably 0.2 to 1.5, from the viewpoint of the avoidance of high vacuum, and from the viewpoint of reduction of the used amount and the recovered amount of at least one of the inert gas and steam. The "flow rate of at least one of the inert gas and steam" is measured under the standard state, i.e. the temperature of 0° C. and the pressure of 101.3 kPa.

It is preferable that the reduction of the odorous components by contacting at least one of the inert gas and steam with the phosphoric ester is carried out under a reduced pressure of at most 20 kPa, from the viewpoint of the efficient reduction of the odorous components. Also, it is desired that the reduction of the odorous components is carried out under reduced pressure of 0.1 to 14 kPa, more preferably under reduced pressure of 1 to 7 kPa, from the viewpoints of the load for an equipment for reducing pressure and the efficient reduction of the odorous components. Also, the temperature is preferably 100° to 160° C., more preferably 120° to 140° C., from the viewpoints of the avoidance of the thermal decomposition of the phosphoric ester and the efficient reduction of the odorous components.

In the present invention, a phosphoric ester having reduced odorous components can be obtained by contacting the phosphoric ester with at least one of an inert gas and steam in a packed tower at 100° to 160° C.

The "packed tower" is intended to refer to a tower in which a packing is packed in its internal. The packed tower has a large vapor-liquid contact area per volume of the apparatus, as compared to those of a rotary thin-film-type evaporator, a multi-step tower and a wetted wall tower. Therefore, the treatment speed for reducing the odorous components can be increased, so that the apparatus itself can be miniaturized. Also, since the packed tower does not have a motor which is necessary for the rotary thin-film-type evaporator, the packed tower is also advantageous in energy efficiency and maintenance.

The packing material used in the packed tower is made of a metal such as stainless steel, titanium or Hastelloy; ceramics; and the like. It is preferable that the packing material has a porosity of 90 to 99% by volume in order to reduce the pressure drop inside the tower.

The kinds of the packing material are not limited to specified ones. As the packing material, there can be used those usually have been used for a rectifying tower and the like. Its kinds are roughly divided into two kinds. One is regular packing, and the other is irregular packing. The regular packing includes one commercially available from Sulzer under the trade name of Sulzer Packing, one commercially available from Julius Montz GmbH under the trade name of Montz Packing, and the like. The irregular packing includes Rashig Ring, Berl Saddle and the like. These packing materials can be used alone or in admixture of at least two kinds. Among them, regular packing is preferable, from the viewpoints of convenience in handling, small pressure drop and the like.

The supplying rate of the phosphoric ester to the packed tower is equal to the treatment rate of the phosphoric ester which is discharged from the packed tower after the treatment. The treatment rate of the packed tower is compared to the treatment rate of the conventional batch-type evaporator or rotary thin-film evaporator in terms of the treatment rate per volume of the contact portion of these apparatuses. The volume of the contact portion is intended to mean the volume of the packed portion in which the packing material is packed as to the packed tower, or the internal volume of the cylinder having a scraping surface at the side surface as to the rotary thin-film-type evaporator.

The flow direction of the phosphoric ester and at least one of the inert gas and steam when the phosphoric ester is contacted with at least one of the inert gas and steam may be any of horizontal flow and vertical flow. Among these flow directions, the vertical flow is preferable, from the viewpoint of the improvement in deodorization efficiency. The flow direction of at least one of the inert gas and steam against the flow direction of the phosphoric ester includes a co-current flow and a countercurrent flow. The countercurrent flow is preferable, from the viewpoint of the improvement in deodorization efficiency by at least one of the inert gas and steam.

From the above viewpoints, it is more preferable that the flow direction of the phosphoric ester and at least one of the inert gas and steam is countercurrent flow in a vertical direction. In addition, it is preferable that the phosphoric ester is supplied to the top of the packed tower, and that the inert gas is supplied to the bottom of the packed tower, from the viewpoint of utilizing free fall of the phosphoric ester inside the packed tower using a gravitational force without any power.

The contact time of the phosphoric ester with at least one of the inert gas and steam cannot be absolutely determined, because the contact time differs depending upon the contacting conditions of the phosphoric ester with at least one of the inert gas and steam, and the like. It is desired that the contact time of the phosphoric ester with at least one of the inert gas and steam is usually 1 to 30 minutes, from the viewpoints of the avoidance of the thermal decomposition of the phosphoric ester and the reduction of the amount of the inert gas necessary for reducing residual odorous components.

Also, it is preferable that the water content in the phosphoric ester is at most 3% by weight, from the viewpoints of the avoidance of the foaming of the phosphoric ester and the corrosion of materials used in the equipments.

In addition, there can be repeated both of a step of heating the phosphoric ester, and contacting the heated phosphoric ester with at least one of the inert gas and steam (hereinafter also referred to as "the step (A)"); and a step of cooling the phosphoric ester having a reduced amount of odorous components obtained in the step (A) (hereinafter also referred to as "the step (B)").

The step (A) is a step which can reduce the odorous components using a general vapor-liquid contact apparatus. The contact apparatus includes, for instance, the above-mentioned packed tower, a rotary thin film-type evaporator disclosed in Japanese Examined Patent Publication No. Sho 57-35595, a wetted wall tower, a falling-film evaporator, a batch-type contact apparatus comprising a blowing tube, plate-type contact apparatus, an ascending film-type contact apparatus, and the like.

Among the contact apparatuses, the batch-type contact apparatus comprising a blowing tube is preferable since this apparatus does not necessitate a specialized apparatus. Also, a rotary thin-film-type evaporator is preferable since the phosphoric ester can be efficiently contacted with at least one of the inert gas and steam, even when the phosphoric ester has a relatively high viscosity. Also, a packed tower is preferable since the contact area of the phosphoric ester with at least one of the inert gas and steam can be increased, so that the amount of odorous components contained in the phosphoric ester can be efficiently reduced. Among them, the packed tower is more preferable.

The flow direction of the phosphoric ester and at least one of the inert gas and steam may be any of horizontal and vertical directions when the phosphoric ester is contacted with at least one of the inert gas and steam. Among these flows, the vertical direction is preferable, from the viewpoint of improving deodorization efficiency. Also, the flow direction of at least one of the inert gas and steam against the flow direction of the phosphoric ester includes co-current flow and countercurrent flow. The countercurrent flow is preferable, from the viewpoint of the improvement in deodorization efficiency by at least one of the inert gas and steam.

From the above, it is more preferable that the flow of the phosphoric ester and at least one of the inert gas and steam is countercurrent flow in a vertical direction. In addition, it is preferable that the phosphoric ester is supplied to the top of the packed tower, and at least one of the inert gas and steam is supplied to the bottom of the packed tower, from the viewpoint of utilizing free fall of the phosphoric ester inside the packed tower with a gravitational force without any power.

In addition, the temperature of the heated phosphoric ester, at which the phosphoric ester is contacted with at least one of the inert gas and steam is preferably 100° to 160° C., more preferably 120° to 140° C., from the viewpoints of the avoidance of the thermal decomposition of the phosphoric ester and the improvement in the reduction of odorous components.

It is preferable that the pressure at which the phosphoric ester is contacted with at least one of the inert gas and steam is reduced to at most 20 kPa, from the viewpoint of efficiently reducing the odorous components in the reduction of the odorous components by contacting the phosphoric ester with at least one of the inert gas and steam. In addition, the pressure is preferably 0.1 to 14 kPa, more preferably 1 to 7 kPa, from the viewpoints of the reduction of a load necessary for an equipment for reducing the pressure and the reduction of the odorous components.

The contact time of the phosphoric ester with at least one of the inert gas and steam cannot be absolutely determined, because the contact time differs depending upon the contacting conditions of the phosphoric ester with at least one of the inert gas and steam, and the like. Usually, the contact time of the phosphoric ester with at least one of the inert gas and steam is preferably 1 to 100 minutes, more preferably 1 to 30 minutes, from the viewpoints of the avoidance of the thermal decomposition of the phosphoric ester and the avoidance of the increase of the amount of at least one of the inert gas and steam for reducing residual odorous components.

In this case, among the inert gas and steam, steam is preferable, because the steam can be easily condensed, so that the load of the thermal energy for the condenser can be reduced and that a load to the exhaust can also be reduced.

Also, it is preferable that the water content in the phosphoric ester is at most 3% by weight, from the viewpoints of the avoidance of the foaming of the phosphoric ester and the corrosion of the materials used in the equipments.

Next, the phosphoric ester contacted with at least one of the inert gas and steam is cooled in the step (B).

It is preferable that the phosphoric ester is cooled as rapidly as possible using a cooling device at the outlet of the contact apparatus, from the viewpoint of the sufficient avoidance of the thermal decomposition of the phosphoric ester. In the cooling device, a general heat exchanger can be used. The cooling device includes, for instance, multipipe-type, double pipe-type, spiral-type and plate-type cooling devices, and any of the cooling devices can be used. The spiral-type cooling device is preferable, from the viewpoints of the miniaturization of its scale and improvement in heat exchange efficiency.

It is preferable that the cooling temperature of the phosphoric ester is at most 90° C., preferably at most 80° C., more preferably at most 60° C., from the viewpoint of the avoidance of the thermal decomposition of the phosphoric ester.

The lower limit of the cooling temperature cannot be absolutely determined because the cooling temperature differs depending upon the kinds of the phosphoric ester.

The phosphoric ester generally has a property of drastically increasing its viscosity with the lowering of its temperature. When the viscosity of the phosphoric ester increases, the pressure inside the cooling device is increased, and the heat exchange efficiency is lowered, and moreover there is a possibility that the operation becomes difficult due to clogging. For this reason, it is preferable that the lower limit of the cooling temperature is a temperature at which the fluidity of the phosphoric ester can be maintained.

The temperature at which the fluidity of the phosphoric ester can be maintained cannot be absolutely determined because the temperature differs depending upon the kinds of organic hydroxy compound. For instance, when a phosphoric ester of an organic hydroxy compound prepared by adding ethylene oxide to an alcohol having 11 carbon atoms to have an average number of moles of ethylene oxide added of 3 is used, it is preferable that the temperature is 5° C.

The excessive cooling of the phosphoric ester is undesirable, from the viewpoint of thermal energy efficiency in the next step (A).

Although the time period required for cooling the phosphoric ester to a desired temperature is not limited to specified ones, it is preferable that the time period is as short as possible, from the viewpoint of the sufficient avoidance of the thermal decomposition of the phosphoric ester. The process for lowering the temperature of the phosphoric ester to a desired temperature in a short time includes, a process comprising lowering the temperature of a refrigerant, a process comprising increasing the area of heat-transfer surface of a heat exchanger, and the like. These processes can be used alone or in combination thereof.

Next, when a tank is charged with the phosphoric ester which is supplied to a contact apparatus, there can be employed a batch operation comprising feeding the cooled phosphoric ester to another tank, and subsequently using the cooled phosphoric ester in the above-mentioned step (A). Alternatively, there can be employed a continuous operation comprising feeding a phosphoric ester which is passed through the contacting apparatus to a tank containing a phosphoric ester which is supplied to the contact apparatus, and the collected phosphoric ester is used in the above-mentioned step (A).

By carrying out the step (A) and the step (B) by the batch operation or continuous operation mentioned above, the amount of the odorous components contained in the phosphoric ester can be reduced.

The number of repetitions for the step (A) and the step (B) cannot be absolutely determined, because the number of repetitions differs depending upon the amount of the odorous components contained in the phosphoric ester, the contact conditions of the phosphoric ester with at least one of the inert gas and steam, and the like. It is preferable that the above steps are repeated until the amount of the odorous components is usually reduced to a desired amount. It is preferable that the cycle composed of the step (A) and the step (B) is usually repeated 1 to 10 times.

Next, the process for preparing a phosphoric ester of the present invention will be described on the basis of a drawing. FIG. 1 is a schematic explanatory view of a process for preparing a phosphoric ester of the present invention.

In the process shown in FIG. 1, the amount of the odorous components contained in the phosphoric ester can be reduced by utilizing a circulation system mainly composed of a tank 1, a feed pump 2, a heating member 3, a packed tower 4 and a cooling portion 9.

First, the phosphoric ester containing the odorous components is introduced into the tank 1.

The phosphoric ester is introduced into the heating member 3 from this tank 1 with the feed pump 2, and the phosphoric ester is heated to a given temperature in the heating member 3.

The phosphoric ester heated to a given temperature in the heating member 3 is introduced into a packed tower 4. In the packed tower 4, the phosphoric ester is contacted with at least one of the inert gas and steam. In this case, it is preferable that the phosphoric ester is introduced to an inlet 5 provided at the top of the packed tower 4, so that the phosphoric ester is fallen down with gravitational force. On the, other hand, it is preferable that at least one of the inert gas and steam is introduced to a gas inlet 6 provided at the lower portion of the packed tower 4, and exhausted from an exhaust out let 7 provided at the upper portion of the packed tower 4. When the phosphoric ester and at least one of the inert gas and steam are introduced into the packed tower 4 in the manner as mentioned above, the contact efficiencies of the phosphoric ester and at least one of the inert gas and steam are increased.

The odorous components contained in the phosphoric ester are removed from the phosphoric ester by the contact of the phosphoric ester with at least one of the inert gas and steam, and incorporated into at least one of the inert gas and steam. Therefore, the odorous components are exhausted together with at least one of the inert gas and the steam from the exhaust outlet 7 to the outside of the packed tower 4.

On the other hand, the phosphoric ester contacted with at least one of the inert gas and steam is discharged from a discharging outlet 8 provided at the lower portion of the packed tower 4, and cooled to a given temperature with the cooling portion 9, so that the phosphoric ester becomes in a state in which the thermal decomposition is sufficiently suppressed with maintaining its fluidity. When the continuous operation is carried out, the cooled phosphoric ester is introduced into a tank 1 via a valve 12, and homogeneously agitated with an agitation impeller 14 rotated with a motor 13.

While the phosphoric ester collected in the tank 1 is sufficiently mixed with the phosphoric ester having been already existed in the tank 1 with the agitation impeller 14 rotated with the motor 13, the phosphoric ester is introduced into the packed tower 4 via a feed pump 2 at the same time, and the same treatment as described above is carried out. When the batch operation is carried out, the cooled phosphoric ester is introduced into the tank 10. When the amount of the odorous components contained in the phosphoric ester collected in the tank 10 is larger than a desired amount, the phosphoric ester is homogeneously agitated with the agitation impeller 14, and the phosphoric ester is again introduced into the packed tower 4 via the feed pump 2, cooled at the cooling portion 9 and then introduced into the tank 1 emptied. This operation is repeatedly carried out until the amount of the odorous components contained in the phosphoric ester is reduced to a desired amount.

The resulting odorous components-reduced phosphoric ester to a desired amount can be collected from the tank 1 or the tank 10 via the feed pump 2 by opening a collecting valve 11.

The odorous components can be also reduced by adding water to the phosphoric ester, and distilling water from the phosphoric ester under reduced pressure.

By adding water to the phosphoric ester and distilling water together with the odorous components from the phosphoric ester under reduced pressure, a phosphoric ester having reduced odor can be obtained. The distilling of water can be carried out by distillation.

The process of adding water to the phosphoric ester can be any of processes of adding water to the phosphoric ester before the distillation of water and a process of adding water to the phosphoric ester with distilling water. The process of adding water with distilling water is preferable, from the viewpoint of the removal of odorous components. Water may be added continuously or intermittently, and it is preferable to continuously add water, from the viewpoint of easiness in the adjustment of the water content.

It is preferable that the weight ratio of the added water to the phosphoric ester, i.e. water/phosphoric ester, is 0.01 to 3. When the weight ratio is within this range, the removal efficiency of odorous components is increased, so that the decomposition and coloration of the phosphoric ester can be reduced. The above-mentioned weight ratio of water to the phosphoric ester is preferably 0.05 to 0.5, more preferably 0.1 to 0.3. When the phosphoric ester previously contains water before addition of water, the amount of water previously contained is included in the amount of water added.

In the present invention, the above-mentioned weight ratio of the water to the phosphoric ester is intended to mean a ratio of the total weight of water to the total weight of the phosphoric ester while water is distilled (hereinafter also referred to as "during the water distillation").

Further, the water content in the phosphoric ester during the water distillation is preferably at most 10% by weight, more preferably at most 5% by weight, still more preferably at most 3% by weight, from the viewpoints of the avoidance of foaming and gelation during the water distillation in the apparatus, and easiness of distillation of water. In addition, the water content in the phosphoric ester during the water distillation is preferably at least 0.01% by weight, more preferably at least 0.1% by weight, from the viewpoint of reducing odor by the treatment of the water distillation. From these viewpoints, the above-mentioned water content is preferably 0.01 to 10% by weight, more preferably 0.1 to 5% by weight, still more preferably 0.1 to 3% by weight.

In addition, as mentioned above, the water distillation can be carried out at a relatively low temperature by carrying out the water distillation under reduced pressure, whereby the decomposition of the phosphoric ester can be suppressed. In the present invention, it is preferable that the water distillation is carried out under a pressure of at most 30 kPa, from the viewpoint of the vapor pressure of the odorous components. In order to lower the temperature during the distillation, avoid the thermal decomposition of the phosphoric ester and remove the odorous components by the water distillation, the pressure is preferably at most 7 kPa, more preferably 1 to 4 kPa.

The temperature during the water distillation is preferably 60° to 150° C., more preferably 80° to 120° C., from the viewpoints of the removal of the odorous components and the avoidance of the decomposition of the phosphoric ester.

The apparatus used in the present invention includes known apparatuses used in distillation methods, and the like. For instance, batch-type distillation can be carried out in an agitation vessel or an apparatus comprising a general distillatory equipped with a thin-film or heat exchanger and a raw material tank. When the thin film or heat exchanger is used, the distillation can be continuously carried out by using a general distillation apparatus. The batch-type distillation method is preferable because the odorous components can be more efficiently reduced.

Also, in the same manner as the process of contacting the above-mentioned phosphoric ester with at least one of the inert gas and steam, a step of heating the phosphoric ester, adding water to the heated phosphoric ester and distilling water under reduced pressure, and a step of cooling the phosphoric ester obtained in the above-mentioned step can be repeated.

In addition, in the preparation of the phosphoric ester, an organic hydroxy compound is reacted with a phosphorylation agent (hereinafter this reaction is referred to as "phosphorylation reaction"), with introducing an inert gas into the mixture of the organic hydroxy compound and the phosphorylation agent.

The process of introducing an inert gas cannot be absolutely determined because the process differs depending upon the embodiments for the phosphorylation reaction. For instance, when the batch-type distillation method is employed, a process comprising introducing an inert gas into a gas phase or a liquid mixture can be cited. The process comprising introducing the inert gas into a liquid mixture is preferable, from the viewpoint of more efficiently reducing the odorous components. The odorous components can also be efficiently reduced by using a gas dispersing device or the like.

The amount of the inert gas introduced is preferably 0.0001 to 0.5 $m^3/(h.kg)$, more preferably 0.0001 to 0.05 $m^3/(h.kg)$ per 1 kg of the total charged amount of the organic hydroxy compound and the phosphorylation agent, from the viewpoints of the avoidance of the excess inert gas, the reduction of the load of the vacuum equipment, and the avoidance of the high vacuum. The term "the amount of the inert gas introduced $(m^3/(h.kg))$" as referred to herein is a flow rate under the standard state of the temperature of 0° C. and the pressure of 101.3 kPa.

The introduction of the inert gas can be carried out at any time so long as the introduction can be carried out during the phosphorylation reaction. For instance, when phosphorus pentoxide is used as the phosphorylation agent, it is preferable that the introduction of the inert gas can be carried out before the addition of phosphorus pentoxide, namely after the termination of the charging of the organic hydroxy compound, from the viewpoint of the avoidance of the coloration due to the incorporation of air. The introduction of the inert gas can be carried out continuously or in plural divided portions. It is preferable that the introduction of the inert gas is carried out continuously, from the viewpoint of the avoidance of the coloration due to the oxidation of the phosphoric ester and continuous removal of the odorous components.

In addition, the reaction temperature of the organic hydroxy compound with the phosphorylation agent is preferably 50° to 130° C., more preferably 70° to 110° C., from the viewpoints of the avoidance of the lowering of the productivity due to a long reaction time, and the reduction of the amount of the inert gas introduced, thereby avoiding unnecessarily high vacuum, and the avoidance of the thermal decomposition of the generated phosphoric ester, thereby preventing the increase of the odorous components and deterioration in the color. The reaction time cannot be absolutely determined because the reaction time differs depending upon the reaction temperature. The reaction time is preferably 5 to 20 hours or so, more preferably 8 to 15 hours or so, from the viewpoint of the reduction of the amount of the residual organic hydroxy compound.

The pressure during the reaction is not limited to specified ones. The pressure is reduced to preferably at most 70 kPa, more preferably at most 20 kPa, still more preferably at most 10 kPa, from the viewpoint of the reduction of the amount of the inert gas introduced, and from the viewpoint of the avoidance of the necessity of the reaction at high temperatures, i.e. the avoidance of the thermal decomposition of the phosphoric ester, thereby preventing the increase of the odorous components and deterioration of color.

The inert gas includes nitrogen gas, argon gas, helium gas, carbon dioxide gas, and the like. Among them, nitrogen gas and carbon dioxide gas are preferable, and nitrogen gas is more preferable.

When the phosphorylation agent used in the present invention contains water as mentioned above, it is preferable that the reaction pressure is controlled after water is not existed in the reaction system, from the viewpoint of the avoidance of the deviation of the molar ratio of the charged phosphoric ester due to the evaporation of water. For instance, when the reaction temperature is 90° C., the deviation of the molar ratio can be prevented by heating the liquid mixture to the desired reaction temperature of 90° C., and controlling the reaction pressure. It is not preferable to use steam since the deviation of the molar ratio of the phosphorylation agent is generated due to the reaction of the steam with the phosphorylation agent during the phosphorylation reaction, and the coloration is not efficiently avoided. The water content in the reaction system can be determined by using a general water content analyzer, for instance, Karl Fischer's device for coulometric titration [commercially available from Hiranuma Sangyo K. K. under the trade name of "AQUACOUNTER AQ-7"].

A pyrophosphoric acid compound derived from the phosphorylation agent is contained in the phosphoric ester thus obtained. It is desired that the phosphoric ester is hydrolyzed by adding water to the phosphoric ester at 50° to 100° C., preferably 70° to 90° C., from the viewpoint of the avoidance of the increase of the odorous components due to this pyrophosphoric acid compound.

Since the phosphoric ester of the organic hydroxy compound obtained by the above process has reduced odor, the phosphoric ester can be suitably used as it is or in the form of a salt in a surfactant composition used for a base material or the like used in the fields of a cleaning agent, an emulsifier, a fiber-treatment agent, an anticorrosive agent and pharmaceuticals, more specifically in a shampoo, a cleaning agent, a facial cleansing agent and the like.

When the concentration of the salt of the phosphoric ester in the surfactant composition becomes higher, the viscosity becomes drastically higher, so that its handling becomes very difficult. However, a surfactant composition comprising (a) at least one compound selected from the group consisting of polyhydric alcohols having 1 to 3 carbon atoms and polyalkylene glycols having a molecular weight of at most 5000, (b) a monohydric alcohol having 1 to 3 carbon atoms, and a salt of (c) the phosphoric ester having reduced odorous components obtained by the process of the present invention would provide a solution having a high concentration of the salt of the phosphoric ester showing a viscosity of at most 3000 mPa.s at a temperature of 30° C. at a shearing rate of 50 $s^{-1}$.

In this case, it is preferable in the surfactant composition that the content of the component (a) is 1 to 30% by weight, that the content of the component (b) is 1 to 8% by weight, and that the content of the component (c) is 50 to 90% by weight.

The component (a) includes polyhydric alcohols having 1 to 3 carbon atoms, such as ethylene glycol and propylene glycol; and polyalkylene glycols, such as polyethylene glycol and polypropylene glycol, having a molecular weight of at most 5000, preferably at most 3000, and preferably at least 300. Among them, dipropylene glycol and polypropylene glycol are preferable. These may be used alone or in admixture of at least two kinds.

The component (b) includes methanol, ethanol, propanol and the like, and ethanol is preferred.

The salt of the phosphoric ester is obtained by neutralizing the phosphoric ester with an alkali substance. The alkali substance includes hydroxides such as sodium hydroxide, potassium hydroxide and ammonium hydroxide; carbonates such as sodium carbonate and potassium carbonate; amines such as monoethanolamine, diethanolamine and triethanolamine; and the like. These alkali substances can be used alone or in admixture of at least two kinds.

The concentration of the alkali substance is not limited to specified ones. The concentration can be arbitrarily adjusted depending upon the effective concentration of the effective component of the desired salt of the phosphoric ester of the organic hydroxy compound, and a solid alkali substance can be also used. An aqueous sodium hydroxide and an aqueous potassium hydroxide are preferable, from the viewpoint of easiness in handling.

The amount of the alkali substance (hereinafter referred to as "degree of neutralization") is 1.0 to 2.0 times, preferably 1.0 to 1.5 times that of the equivalent amount of the phosphoric ester. When the amount is at least 1.0 time that of the equivalent amount of the phosphoric ester, the stability of the salt of the phosphoric ester is improved at low temperatures. When the amount is at most 2.0 times that of the equivalent amount of the phosphoric ester, strong basicity is not imparted to the salt of the phosphoric ester, so that handling becomes facilitated, and the corrosion of the equipments can be avoided.

Besides the component (a), the component (b) and the component (c), the above-mentioned surfactant component may contain water, phosphoric acid, an organic hydroxy compound, and the like. Water means the water derived from the water generated during the neutralization of an acidic phosphoric ester, water added and the like. It is preferable that water is contained in the surfactant composition, from the viewpoints of reducing the viscosity of the surfactant composition and increasing the flash point.

Also, in this surfactant composition, other components can be added as occasion demands. The other components include, for instance, antioxidants such as dibutylhydroxytoluene and butylhydroxyanisole; anticorrosive agents such as methylparaben; hypochlorites such as sodium hypochlorite and potassium hypochlorite; decoloring agents such as hydrogen peroxide; metal chelating agents such as ethylenediaminetetraacetate; pH buffers; and the like.

EXAMPLE I

Example I-1

Step A

The amount 287.5 g (0.95 mol) of an ethylene oxide-added undecyl alcohol formed by adding 3 mol of ethylene oxide to 1 mol of undecyl alcohol (commercially available from Shell Oil Company under the trade name of Neodol 1-3) was mixed with 22.2 g of an 85% aqueous phosphoric acid (the amount of phosphorus peroxide being 0.096 mol and the amount of water being 0.474 mol), and 54.3 g (0.377 mol) of phosphorous pentoxide was gradually added to the resulting mixture, with maintaining the temperature of 40° to 50° C. Thereafter, the temperature was increased to 80° C., and the mixture was reacted for 12 hours. Thereafter, 18.2 g of ion-exchanged water was added thereto at 80° C. for 3 hours, to give a phosphoric ester.

Step B

Next, this phosphoric ester was continuously supplied at a rate of 30 g/min. to the top of a packed tower [inner diameter: 50 mm, height: 22 cm, packing material: an article commercially available from SUMITOMO HEAVY METAL INDUSTRIES, LTD. under the trade name of Sulzer-Labopacking] of which pressure was controlled to 4 kPa, with increasing the temperature of the mixture to 130° C. To the bottom of the tower, steam was supplied at a rate of 15 g/min. at 90° C. to countercurrent-contact the phosphoric ester with the steam. After the contact time of 3 minutes passed, a phosphoric ester having a reduced amount of odorous components was obtained from the bottom of the tower.

Example I-2

Step A

The phosphorylation reaction was carried out in the same manner as in the step A of Example I-1 except that 262.5 g (1.411 mol) of dodecyl alcohol, 24.1 g of an 85% aqueous phosphoric acid (the amount of phosphorus pentoxide being 0.105 mol and the amount of water being 0.514 mol), and 77.4 g (0.545 mol) of phosphorous pentoxide were used in place of undecyl alcohol and the 85% aqueous phosphoric acid used in the step A of Example I-1, and that ion-exchanged water was not added, to give a phosphoric ester.

Step B

The phosphoric ester obtained in the step A was continuously supplied at a rate of 30 g/min. to the top of a packed tower [inner diameter: 50 mm, height: 55 cm, packing material: an article commercially available from SUMITOMO HEAVY METAL INDUSTRIES, LTD. under the trade name of Sulzer-Labopacking] of which pressure was controlled to 4 kPa, with increasing the temperature of the mixture to 130° C. To the bottom of the tower, steam was supplied at a rate of 10 g/min. at 90° C. to countercurrent-contact the phosphoric ester with the steam. After the contact time of 8 minutes passed, a phosphoric ester having a reduced amount of odorous components was obtained from the bottom of the tower.

Example I-3

The same procedures as in Example I-1 were carried out except that an irregular packing [outer diameter: 6 mm, opening size: 100 mesh (Tyler mesh), commercially available from Sankyo Tokushu Kinzoku Kako K.K. under the trade name: McMahon Packing] as a packing material used in the step B of Example I-1, to give a deodorized product.

Example I-4

The phosphoric ester obtained in the same manner as in the step A of Example I-1 was countercurrent-contacted with the steam under the conditions of temperature of 100° C., pressure of 1 kPa, contact time of 8 minutes and a steam flow rate of 21 g/min. in the packed tower used in the step B of Example I-2, and a phosphoric ester having a reduced amount of odorous components was obtained from the bottom of the tower.

Example I-5

The same procedures as in Example I-1 were carried out except that the pressure of the packed tower was changed to 20 kPa in the step B of Example I-1, to give a phosphoric ester having a reduced amount of odorous components.

Comparative Example I-1

A 500 mL batch-type evaporator (four-necked flask) equipped with a tube for blowing steam was charged with 200 g of the phosphoric ester obtained in the same manner as in the step A of Example I-1 (evaluation of odor being 6), and the temperature was increased to 100° C. under the pressure of 2.7 kPa. Thereafter, steam was blown into the batch-type evaporator at 90° C. and at a flow rate of 100 g/h for 3 hours, to give a phosphoric ester having a reduced amount of odorous components.

Comparative Example I-2

The same procedures as in Example I-1 were carried out except that the contact temperature of the phosphoric ester with the steam in the packed tower was changed from 130° C. to 170° C. in the step B of Example I-1, to give a phosphoric ester having a reduced amount of odorous components.

Comparative Example I-3

The same procedures as in Example I-1 were carried out except that the contact temperature of the phosphoric ester with the steam in the packed tower was changed from 130° C. to 90° C. in the step B of Example I-1, to give a phosphoric ester having a reduced amount of odorous components.

Comparative Example I-4

The same procedures as in Example I-1 were carried out except that a rotary thin-film-type evaporator [commercially available from Shinko Pantec Co., Ltd. under the model number of 2-03, area of heat-conduction surface: 0.03 m$^2$, made of glass] was used in place of the packed tower used in the step B of Example I-1, that the supplying rate of the phosphoric ester was changed to 3 g/min., that the supplying rate of the steam was changed to 1.5 g/min., that the contact time was changed to 1 minute, that the pressure was changed to 4 kPa, and that the rotational speed of the scraper was changed to 400 r/min., to give a phosphoric ester having a reduced amount of odorous components.

Next, the evaluation of odor and the evaluation of hue were carried out for the phosphoric ester obtained in the step A of each Example and each Comparative Example (phosphoric ester before the treatment) and the phosphoric ester having a reduced amount of odorous components obtained in the step B (phosphoric ester after the treatment) in accordance with the following methods. The results are shown in Table 1.

Evaluation of Odor

A 110 mL glass standard jar was charged with 50 mL of the phosphoric ester before or after the treatment, one expert panelist directly smells the odor at the opening of the jar. The strength of the odor was ranked in 7 stages of 0 to 6, where 0 is defined as no odor and 6 as the strongest odor, and the evaluation was determined with the senses depending upon the strength of the odor. Rank 0 means no odor, and odor with a rank of at most 3 is serviceable level.

Evaluation of Hue

A silica glass cell was charged with a solution prepared by diluting the phosphoric ester before or after the treatment with ethanol to a concentration of 10% by weight, and absorbance was determined with a spectrophotometer [commercially available from Shimadzu Corporation under the trade name of UV-1600] at a wavelength of 420 nm, and the resulting value was multiplied by a factor of 1000.

TABLE 1

| Example No. | I-1 | I-2 | I-3 | I-4 | I-5 |
|---|---|---|---|---|---|
| Organic Hydroxy Compound | | | | | |
| Number of Carbon Atoms | 11 | 12 | 11 | 11 | 11 |
| Number of Moles of Ethylene Oxide Added | 3 | 0 | 3 | 3 | 3 |
| Contact Conditions | | | | | |
| Apparatus | Packed Tower (Regular Packing) | Packed Tower (Regular Packing) | Packed Tower (Irregular Packing) | Packed Tower (Regular Packing) | Packed Tower (Regular Packing) |
| Contact Temp. [° C.] | 130 | 130 | 130 | 100 | 130 |
| Pressure [kPa] | 4 | 4 | 4 | 1 | 20 |
| Ratio of Flow Rates of Inert Gas/Phosphoric Ester (m$^3$ (standard state)/h)/(kg/h) | 0.62 | 0.37 | 0.62 | 0.87 | 0.62 |
| Contact Time [min.] | 3 | 8 | 3 | 8 | 3 |
| Treating Rate [g/min.] | 30 | 30 | 30 | 30 | 30 |
| Volume of Contacted Portion [L] | 0.43 | 1.08 | 0.43 | 1.08 | 0.43 |
| Treating Rate per Volume of Contacted Portion [g/(min. · L)] | 69.5 | 27.8 | 69.5 | 27.8 | 69.5 |
| Evaluation of Odor | | | | | |
| Before Treatment | 6 | 6 | 6 | 6 | 6 |
| After Treatment | 2 | 2 | 2 | 3 | 4 |

TABLE 1-continued

| Evaluation of Hue | | | | | |
|---|---|---|---|---|---|
| Before Treatment | 4 | 4 | 4 | 4 | 4 |
| After Treatment | 4 | 5 | 4 | 4 | 4 |

| Comparative Example No. | I-1 | I-2 | I-3 | I-4 |
|---|---|---|---|---|
| Organic Hydroxy Compound | | | | |
| Number of Carbon Atoms | 11 | 11 | 11 | 11 |
| Number of Moles of Ethylene Oxide Added | 3 | 3 | 3 | 3 |
| Contact Conditions | | | | |
| Apparatus | Batch-Type Evaporator | Packed Tower (Regular Packing) | Packed Tower (Regular Packing) | Rotary Thin-Film-Type Evaporator |
| Contact Temp. [° C.] | 100 | 170 | 90 | 130 |
| Pressure [kPa] | 2.7 | 4 | 4 | 4 |
| Ratio of Flow Rates of Inert Gas/Phosphoric Ester (m$^3$ (standard state)/h)/(kg/h) | 1.86 | 0.62 | 0.62 | 0.62 |
| Contact Time [min.] | 180 | 3 | 3 | 1 |
| Treating Rate [g/min.] | 2.2 | 30 | 30 | 3 |
| Volume of Contacted Portion [L] | 0.5 | 0.43 | 0.43 | 0.47 |
| Treating Rate per Volume of Contacted Portion [g/(min. · L)] | 4.4 | 69.5 | 69.5 | 6.3 |
| Evaluation of Odor | | | | |
| Before Treatment | 6 | 6 | 6 | 6 |
| After Treatment | 4 | 6 | 5 | 3 |
| Evaluation of Hue | | | | |
| Before Treatment | 4 | 4 | 4 | 4 |
| After Treatment | 10 | 300 | 4 | 4 |

From the results shown in Table 1, it can be seen that according to each Example, phosphoric esters having reduced odor and excellent hue can be obtained at a large treatment rate.

On the other hand, since a batch-type evaporator or a rotary thin-film-type evaporator is used in Comparative Example I-1 or I-4, it can be seen that the treatment rate is small. Also, since the contact temperature is high in Comparative Example I-2, it can be seen that the evaluation of odor and the evaluation of hue are remarkably low. Since the contact temperature is low in Comparative Example I-3, it can be seen that the evaluation of odor is little improved.

According to the process of each Example, as compared to the case where the batch-type evaporator or rotary thin-film-type evaporator having the same scale was used, the odorous components can be reduced at a higher removal treatment rate, and a phosphoric ester being excellent in the evaluation of odor and evaluation of hue can be easily obtained.

In addition, according to the process of each Example, when the treatment rate is constant, there can be easily prepared a phosphoric ester having excellent hue because the odor can be efficiently reduced by using a packed tower which is smaller than conventional rotary thin-film evaporators.

EXAMPLE II

Example II-1

Preparation of Phosphoric Ester

The amount 862.5 g (2.85 mol) of an ethylene oxide-added undecyl alcohol formed by adding 3 mol of ethylene oxide to 1 mol of undecyl alcohol (commercially available from Shell Oil Company under the trade name of Neodol 13) was mixed with 66.6 g of an 85% aqueous phosphoric acid (the amount of phosphorus pentoxide being 0.288 mol and the amount of water being 1.422 mol), and 162.9 g (1.13 mol) of phosphorous pentoxide was gradually added to the resulting mixture, with maintaining the temperature of 40° to 50° C. Thereafter, the temperature was increased to 80° C., and the mixture was reacted for 12 hours. Thereafter, 54.6 g of ion-exchanged water was added thereto at 80° C. for 3 hours, to give a phosphoric ester.

The evaluation of odor of the resulting phosphoric ester (evaluation of odor of initial phosphoric ester) was carried out in the same manner as in Example I. The results are shown in Table 2.

Step A (First Time)

As shown in FIG. 1, there was used an apparatus comprising a 2-L tank 1, a 2-L tank 10, and a packed tower [inner diameter: 50 mm, height: 22 cm, packing material: an article commercially available from SUMITOMO HEAVY METAL INDUSTRIES, LTD. under the trade name of Sulzer-Labopacking: 4 Element] 4, in which the tank 1, the tank 10 and the packed tower 4 were connected with pipes.

Five-hundred grams of the phosphoric ester obtained as described above was introduced into the tank 1. With increasing the temperature of the phosphoric ester supplied to the bottom of this tank 1 to 130° C. with a heating member 3 via a feed pump 2, the phosphoric ester was continuously supplied at a flow rate of 25 g/min. to the packed tower 4, and the pressure at the top of the tower was controlled to 4 kPa. At the same time, the steam was supplied to the bottom of the packed tower 4 at a flow rate of 5 g/min., thereby countercurrent-contacting the phosphoric ester with the steam at 130° C. for a one-pass contact time of 3 minutes. Thereafter, the resulting phosphoric ester was discharged from a discharging outlet 8 at the bottom of the tower. The term "one-pass contact time" is intended to mean a time period while the phosphoric ester is contacted with the steam in the internal of the packed tower 4 until the phosphoric ester which is supplied to an inlet 5 at the top of the packed tower is discharged from a discharging outlet 8 at the lower portion of the packed tower 4.

Step B

The phosphoric ester discharged in the step A was continuously cooled to 60° C. at a cooling portion 9 and returned to the tank 1.

Second Step A

With mixing the returned phosphoric ester with the phosphoric ester existing in the tank 1, the phosphoric ester was supplied from the bottom of the tank 1 to the packed tower 4 via a feed pump 2 in the same manner as described above, and the phosphoric ester was countercurrent-contacted with the steam at 130° C. for a one-pass contact time of 3 minutes.

The second step A and the step B were repeated. The repeating time period was 40 minutes from the beginning of the first step A.

The average contact time, which is a contact time period while the whole of the initial phosphoric ester contained in the tank 1 is contacted with the steam in the step A, was 6 minutes. In addition, the average heating time at 130° C. was 6 minutes, which is the same as the average contact time, since the cooling procedures were carried out after the termination of the step A. The average contact time is obtained in accordance with the following equation (I):

[Average Contact Time]=[Entire Circulation Amount]÷[Amount of Initial Phosphoric Ester]×[One-Pass Contact Time]   (I)

In this Example, since the phosphoric ester was circulated at a rate of 25 g/min. for 40 minutes, the entire circulation amount was 1000 g, and the amount of the initial phosphoric ester was 500 g.

The phosphoric ester having reduced odorous components thus obtained was taken out from a valve 11, and the evaluation of odor (evaluation of odor of the phosphoric ester after the treatment) was carried out in the same manner as described above. The results are shown in Table 2.

Example II-2

The same procedures as in Example II-1 were carried out except that the phosphoric ester discharged in the step A was returned to the tank 10 by switching a valve 12 in place of returning the phosphoric ester to the tank 1, the returned phosphoric ester was supplied again from the bottom of the tank 10 to the packed tower 4 via a feed pump 2, and thereafter the phosphoric ester was returned to the tank 1 in the step B of Example II-1, which is a so-called batch operation system, to give a phosphoric ester.

The evaluation of odor of the resulting phosphoric ester having reduced odorous components was carried out in the same manner as in Example I. The results are shown in Table 2.

Example II-3

Preparation of Phosphoric Ester

The same procedures as in Example II-1 were carried out except that 840.0 g (4.516 mol) of dodecyl alcohol, 77.2 g of an 85% aqueous phosphoric acid (the amount of phosphorus pentoxide being 0.336 mol and the amount of water being 1.644 mol), and 251.4 g (1.744 mol) of phosphorous pentoxide were used in place of 862.5 g (2.85 mol) of undecyl alcohol, 66.6 g of the 85% aqueous phosphoric acid and 162.9 g (1.13 mol) of phosphorus pentoxide used in Example II-1, and that ion-exchanged water was not added, to give a phosphoric ester.

The evaluation of odor of the resulting phosphoric ester having reduced odorous components was carried out in the same manner as in Example I. The results are shown in Table 2.

Step A and Step B

The same procedures as in Example II-1 were carried out except that the phosphoric ester obtained as described above was used, that the one-pass contact time was changed from 3 minutes to 6 minutes in the step A of Example II-1, so that each of the average contact time and the average heating time was changed to 12 minutes, respectively, and that the cooling temperature was changed from 60° C. to 80° C., to give a phosphoric ester.

The evaluation of odor of the resulting phosphoric ester having reduced odorous components was carried out in the same manner as in Example I. The results are shown in Table 2.

Example II-4

The same procedures as in Example II-1 were carried out except that an irregular packing [outer diameter: 6 mm, opening size: 100 mesh (Tyler mesh), commercially available from Sankyo Tokushu Kinzoku Kako K.K. under the trade name: McMahon Packing] as a packing material to be packed in the packed tower 4 in the step A of Example II-1, to give a phosphoric ester.

The evaluation of odor of the resulting phosphoric ester having reduced odorous components was carried out in the same manner as in Example I. The results are shown in Table 2.

Example II-5

The same procedures as in Example II-1 were carried out except that a rotary thin-film-type evaporator commercially available from Shinko Pantec Co., Ltd. under the model number of 2-03 [area of heat-conduction surface: 0.03 m$^2$, made of glass] was used in place of the packed tower 4 used in the step A of Example II-1, and that the one-pass contact time of the phosphoric ester with the steam was changed to 2 minutes in the step A, so that each of the average contact time and the average heating time was changed to 4 minutes, respectively, to give a phosphoric ester.

The evaluation of odor of the resulting phosphoric ester having reduced odorous components was carried out in the same manner as in Example I. The results are shown in Table 2.

Example II-6

The same procedures as in Example II-1 were carried out except that a batch-type contact apparatus [made of glass, 2 L four-necked flask, equipped with a tube for blowing steam] was used in place of the packed tower 4, that the amount of the phosphoric ester introduced into the tank 1 was changed to 1000 g, the contact temperature to 100° C., the pressure to 2 kPa, and the flow rate of the steam to 12.5 g/min., so that the ratio of the flow rate of an inert gas to that of the phosphoric ester was changed to 0.5, and that the one-pass contact time from the supply of the phosphoric ester into the batch-type contact apparatus to the discharge of the phosphoric ester was changed to 30 minutes in the step A of Example II-1, and that the repeating time period for the step A and the step B was changed to 120 minutes, so that each of the average contact time and the average heating time was changed to 90 minutes, respectively, to give a phosphoric ester.

The evaluation of odor of the resulting phosphoric ester having reduced odorous components was carried out in the same manner as in Example I. The results are shown in Table 2.

Comparative Example II-1

The same procedures as in Example II-1 were carried out except that the phosphoric ester was kept at 130° C. without cooling the phosphoric ester to 60° C. with the cooling member 9 in the step B of Example II-1, to give a phosphoric ester. Since the temperature of the phosphoric ester was also 130° C. in the step B, the average heating time was 40 minutes, which was the same as the repeating time period.

The evaluation of odor of the resulting phosphoric ester having reduced odorous components was carried out in the same manner as in Example I. The results are shown in Table 2.

Comparative Example II-2

The same procedures as in Example II-6 were carried out except that the phosphoric ester was kept at 100° C. without cooling the phosphoric ester to 60° C. with the cooling member 9 in the step B of Example II-6, to give a phosphoric ester. Since the temperature of the phosphoric ester was also 100° C. in the step B, the average heating time was 120 minutes, which was the same as the repeating time period.

The evaluation of odor of the resulting phosphoric ester having reduced odorous components was carried out in the same manner as in Example I. The results are shown in Table 2.

TABLE 2

| | Example No. | | | |
|---|---|---|---|---|
| | II-1 | II-2 | II-3 | II-4 |
| Organic Hydroxy Compound | | | | |
| Number of Carbon Atoms | 11 | 11 | 12 | 11 |
| Number of Moles of Ethylene Oxide Added | 3 | 3 | 0 | 3 |
| Contact Conditions | | | | |
| Apparatus | Packed Tower (Regular Packing) | Packed Tower (Regular Packing) | Packed Tower (Regular Packing) | Packed Tower (Irregular Packing) |
| Contact Temp. (° C.) | 130 | 130 | 130 | 130 |
| Pressure (kPa) | 4 | 4 | 4 | 4 |
| Ratio of Flow Rates of Inert Gas/Phosphoric Ester (m³/h)/(kg/h) | 0.25 | 0.25 | 0.25 | 0.25 |
| Average Contact Time (min.) | 6 | 6 | 12 | 6 |
| Average Heating Time (min.) | 6 | 6 | 12 | 6 |
| Operation | Continuous | Batch | Continuous | Continuous |
| Cooling Conditions: Cooling Temperature (° C.) | 60 | 60 | 80 | 60 |
| Evaluation of Odor | | | | |
| Initial | 6 | 6 | 6 | 6 |
| After Treatment | 2 | 2 | 2 | 2 |

| | Example No. | | Comparative Example No. | |
|---|---|---|---|---|
| | II-5 | II-6 | II-1 | II-2 |
| Organic Hydroxy Compound | | | | |
| Number of Carbon Atoms | 11 | 11 | 11 | 11 |
| Number of Moles of Ethylene Oxide Added | 3 | 3 | 3 | 3 |
| Contact Conditions | | | | |
| Apparatus | Rotary Thin-Film-Type | Batch-Type Contact Apparatus | Packed Tower (Regular | Batch-Type Contact Apparatus |

TABLE 2-continued

| | Evaporator | | Packing) | |
|---|---|---|---|---|
| Contact Temp. (° C.) | 130 | 100 | 130 | 100 |
| Pressure (kPa) | 4 | 2 | 4 | 2 |
| Ratio of Flow Rates of Inert Gas/Phosphoric Ester (m³/h)/(kg/h) | 0.25 | 0.5 | 0.25 | 0.5 |
| Average Contact Time (min.) | 4 | 90 | 6 | 90 |
| Average Heating Time (min.) | 4 | 90 | 40 | 120 |
| Operation | Continuous | Continuous | Continuous | Continuous |
| Cooling Conditions: Cooling Temperature (° C.) | 60 | 60 | None | None |
| Evaluation of Odor | | | | |
| Initial | 6 | 6 | 6 | 6 |
| After Treatment | 2 | 3 | 5 | 5 |

From the results shown in Table 2, it can be seen that according to each Example, since the operation comprising heating a phosphoric ester, contacting the heated phosphoric ester with an inert gas, and thereafter cooling the phosphoric ester is repeated, the odorous components contained in the phosphoric ester are efficiently removed.

EXAMPLE III

Preparation Example III-1

The amount 819.8 g (4.40 mol) of lauryl alcohol was mixed with 75.0 g of an 85% by weight aqueous orthophosphoric acid [46.2 g (0.32 mol) of $P_2O_5$ and 28.8 g (1.60 mol) of $H_2O$, when the orthophosphoric acid is represented by $P_2O_5 \cdot nH_2O$] with stirring in a 2000 mL reaction vessel. Thereto was gradually added 247.4 g (1.74 mol) of phosphorus pentoxide (effective content: 98.5% by weight), with maintaining the temperature of the mixture at 60° to 70° C. Thereafter, the temperature of the mixture was increased to 80° C., and the reaction was carried out for 12 hours. The value for the formula (1) was 2.9. The resulting phosphoric ester had an evaluation of odor of 5, showing strong odor, thereby making it impossible to use the phosphoric ester in a cleaning agent and the like.

Example III-1

The amount 253 g of the phosphoric ester obtained in Preparation Example III-1 was transferred to an evaporator of a 500 mL of a batch-type agitation vessel to which water could be continuously added. After the pressure was reduced to 2.7 kPa, the temperature was increased to 90° C. With stirring, the distillation was carried out with continuously adding water at a rate of 20 g/h to the phosphoric ester for 2 hours (total water content: 40 g). The water content of the phosphoric ester was determined. As a result, the water content was 0.2 to 1.0% by weight.

The evaluation for odor of the phosphoric ester obtained by this operation was carried out in the same manner as described above. As a result, the evaluation of odor was 2, showing little odor.

The water content of the phosphoric ester was determined by using Karl Fischer's device for coulometric titration [commercially available from Hiranuma Sangyo K.K. under the trade name of "AQUACOUNTER AQ-7"].

Comparative Example III-1

The same procedures as in Example III-1 were carried out except that the same apparatus as used in Example III-1 was charged with 250 g of the phosphoric ester obtained in Preparation Example III-1, and that water was not added during distillation. No water content was detected during the distillation. The resulting phosphoric ester had an evaluation of odor of 5, showing strong odor, which is not different from the odor before the distillation, thereby making it impossible to use the phosphoric ester in a cleaning agent and the like.

Comparative Example III-2

The procedures were carried out under the same conditions as in Example III-1 except that the same apparatus as used in Example III-1 was charged with 250 g of the phosphoric ester obtained in Preparation Example III-1, and that addition of water was changed to the blowing of steam into the liquid mixture. Specifically, after the pressure was reduced to 2.7 kPa, the temperature was increased to 90° C. With stirring, the distillation was carried out with continuously adding the steam at a rate of 20 g/h to the phosphoric ester for 2 hours (total water content: 40 g). The water content of the phosphoric ester was determined. As a result, the water content was 0.3 to 1.1% by weight. The resulting phosphoric ester had an evaluation of odor of 4, which showed that the odor was slightly improved. However, since the phosphoric ester showed strong odor, it is impossible to use the phosphoric ester in a cleaning agent and the like.

In order to have the sensory evaluation of the phosphoric ester obtained as mentioned above to be ranked at a serviceable level of "3," blowing steam should be carried out for additional 10 hours for deodorizing the phosphoric ester.

Preparation Example III-2

The amount 287.5 g (0.95 mol) of an ethylene oxide-added undecyl alcohol formed by adding 3 mol of ethylene oxide to 1 mol of undecyl alcohol (commercially available from Shell Oil Company under the trade name of Neodol 1-3) was mixed with 22.2 g of an 85% by weight aqueous phosphoric acid [13.7 g (0.096 mol) of $P_2O_5$ and 8.5 g (1.60 mol) of $H_2O$, when the phosphoric acid is represented by $P_2O_5 \cdot nH_2O$] in a 1000 mL apparatus equipped with an agitation device, capable of carrying out the reaction, distillation and continuous addition of water, with stirring. Thereto was gradually added 54.3 g (0.38 mol) of phosphorus pentoxide (effective content: 98.5% by weight), with maintaining the temperature of the mixture at 40° to 50° C. Thereafter, the temperature of the mixture was increased to 80° C., and the reaction was carried out for 12 hours. The value for the formula (1) was 3.0. The resulting phosphoric ester had an evaluation of odor of 6, showing strong odor, thereby making it impossible to use the phosphoric ester in a cleaning agent. Thereafter, 15 g of water was added to the phosphoric ester (water content of the phosphoric ester being 4.0% by weight) to hydrolyze the phosphoric ester at 80° C. under normal pressure for 2 hours.

Example III-2

After the pressure was reduced to 2.0 kPa, the temperature of the phosphoric ester obtained in Preparation Example III-2 was increased to 80° C. With stirring, the distillation was carried out with continuously adding water at a rate of 25 g/h to the phosphoric ester for 5 hours (total water content: 125 g). The water content of the phosphoric ester was determined. As a result, the water content was 0.8 to 2.7% by weight.

The phosphoric ester obtained by this operation had an evaluation for odor of 3, showing reduced odor.

Preparation Example III-3

The reaction was carried out using an apparatus comprising a system for conveying the liquid components from a 2000 mL reaction vessel to a falling-film evaporator with a pump to carry out the distillation under reduced pressure. Thereafter, the liquid components were returned to the above reaction vessel. First, 931.5 g (5.00 mol) of lauryl alcohol was mixed with 117.2 g of an 85% by weight aqueous orthophosphoric acid [72.4 g (0.51 mol) of $P_2O_5$ and 45.1 g (2.50 mol) of $H_2O$, when the orthophosphoric acid is represented by $P_2O_5.nH_2O$] in the reaction vessel with stirring. Thereto was gradually added 292.4 g (2.03 mol) of phosphorus pentoxide (effective content: 98.5% by weight), with maintaining the temperature of the mixture at 60° to 70° C. Thereafter, the temperature of the mixture was increased to 80° C., and the reaction was carried out for 12 hours. The value for the formula (1) was 2.95. The resulting phosphoric ester had an evaluation of odor of 5, showing strong odor, thereby making it impossible to use the phosphoric ester in a cleaning agent and the like.

Example III-3

The pressure inside the apparatus was reduced to 2.7 kPa, with continuously adding water to the reaction vessel at a rate of 53 g/h, and the phosphoric ester obtained in Preparation Example III-3 was conveyed to a falling-film evaporator with a pump at a rate of 30 kg/h to carry out the distillation. The distillation was carried out for 5 hours with controlling the temperature inside the reaction vessel to 50° to 60° C. and the temperature at the outlet of the falling-film evaporator to 100° C. (total water content: 265 g). The water content of the phosphoric ester was determined. As a result, the water content was 1.0 to 2.0% by weight.

The phosphoric ester obtained by this operation had an evaluation for odor of 2, showing reduced odor.

EXAMPLE IV

Example IV-1

The amount 548 g (1.84 mol) of ethoxylate of a higher alcohol having 11 carbon atoms, a branched ratio of 20%, and an average number of moles of ethylene oxide (EO) added of 3 (commercially available from Shell Oil Company under the trade name of Neodol 1-3, molecular weight: 298.6) was mixed with 43 g of an 85% aqueous phosphoric acid (the amount of phosphorus pentoxide being 0.19 mol and the amount of water being 0.92 mol). Next, nitrogen gas was introduced into its gas phase at a rate of 1300 mL/min. (0.11 $m^3$/(h.kg): standard state), and 109 g (0.76 mol) of phosphorous pentoxide was gradually added to the resulting mixture at a temperature of 40° to 70° C. The temperature was increased to 90° C. When water was no longer present in the reaction system, the mixture was reacted under the pressure of 101.3 kPa for 8 hours. Thereafter, 14.0 g of ion-exchanged water was added thereto to hydrolyze the phosphoric ester at 90° C. for 3 hours.

Example IV-2

The amount 548 g (1.84 mol) of ethoxylate of a higher alcohol having 11 carbon atoms, a branched ratio of 20%, and an average number of moles of ethylene oxide (EO) added of 3 (commercially available from Shell Oil Company under the trade name of Neodol 1-3, molecular weight: 298.6) was mixed with 43 g of an 85% aqueous phosphoric acid (the amount of phosphorus pentoxide being 0.19 mol and the amount of water being 0.92 mol). Next, nitrogen gas was introduced into the mixture at a rate of 140 mL/min. (0.012 $m^3$/(h.kg): standard state), and 109 g (0.76 mol) of phosphorous pentoxide was gradually added to the resulting mixture at a temperature of 40° to 70° C. The temperature was increased to 90° C. When water was no longer present in the reaction system, the pressure was reduced to 2.67 kPa, and the mixture was reacted for 8 hours. Thereafter, 14.0 g of ion-exchanged water was added thereto under normal pressure to hydrolyze the phosphoric ester at 90° C. for 3 hours.

Example IV-3

The same phosphorylation reaction as in Example IV-1 was carried out except that the pressure during the phosphorylation was changed to 50 kPa.

Example IV-4

The same phosphorylation reaction as in Example IV-1 was carried out except that the amount of nitrogen gas introduced was changed to 3000 mL/min. (0.26 $m^3$/(h.kg): standard state).

Comparative Example IV-1

The same phosphorylation reaction as in Example IV-1 was carried out except that nitrogen gas was not introduced after the ethoxylate of a higher alcohol was mixed with an 85% aqueous phosphoric acid.

Comparative Example IV-2

The same phosphorylation reaction as in Example IV-3 was carried out except that nitrogen gas was not introduced.

Determination of Amounts of Phosphoric Monoester, Phosphoric Diester and Orthophosphoric Acid A one-gram sample was accurately weighed, and 100 mL of ethanol and 50 mL of water were added to the sample to dissolve the sample. Potentiometric titration was carried out using a ½ N aqueous potassium hydroxide, and a first equivalence point (AV1) and a second equivalence point (AV2) were determined.

Next, about 20 mL of a 2 N aqueous potassium chloride was added to a sample solution prepared by accurately weighing a 1 g sample, and adding 100 mL of ethanol and 50 mL of water thereto to dissolve the sample. Potentiometic titration was carried out using a ½ N aqueous potassium hydroxide, and a third equivalence point (AV3) was determined. The amounts of the phosphoric monoester, the phosphoric diester and the orthophosphoric acid were calculated in accordance with the following equations (2) to (4):

[Amount of Orthophosphoric Acid (% by weight)]=(AV3−AV2)× 98/56108  (2)

[Phosphoric Diester (% by weight)]=(2·AV1−AV2)×[Molecular Weight of Phosphoric Diester]/56108  (3)

[Phosphoric Monoester (% by weight)]=(2·AV2−AV1−AV3)×[Molecular Weight of Phosphoric Monoester]/56108  (4)

Determination of Petroleum Ether-Soluble Component

A five-gram sample was accurately weighed, and thereto were added a petroleum ether, ethanol and a 15% by volume aqueous triethanolamine in the amount of 100 mL respectively in a 500 mL separatory funnel, and the mixture was allowed to separate into layers (A). The resulting lower layer was taken out from the layers and added to another 500 mL separatory funnel. The amount 100 mL of the petroleum ether was added thereto, and the mixture was allowed to separate into layers (B). In the same manner as in the above (A), the lower layer of the above (B) was allowed to separate into layers (C). Each of the upper layers of the above (A), (B) and (C) was mixed together, and the mixture was washed twice with a 50% by volume aqueous ethanol solution, and thereafter the petroleum ether was evaporated in a hot bath at 60° C., to give an extracted petroleum ether-soluble component. The amount of the petroleum ether-soluble component was calculated by the equation (5). The term "petroleum ether-soluble component" as referred to herein means unreacted organic hydroxy compounds and compounds derived from organic hydroxy compounds, containing odorous components.

[Amount of Petroleum Ether-Soluble Component (%)]=[Weight of Extracted Petroleum Ether-Soluble Content (g)]/[Sample Weight (g)]×100  (5)

Hue

The hue was determined in the same manner as in Example I.

Evaluation of Odor

A sample was neutralized with a 48% aqueous potassium hydroxide so that the content of effective ingredients became 27%, the effective ingredients being the phosphoric monoester and the phosphoric diester, and its content being based on the phosphoric ester.

A 110 mL glass standard jar was charged with 50 mL of a salt of this phosphoric ester, and one expert panelist directly smells the odor at the opening of the jar. The strength of the odor was ranked in 7 stages of 0 [no odor] to 6 [strongest odor].

TABLE 3

|  | Example No. | | | | Comparative Example No. | |
| --- | --- | --- | --- | --- | --- | --- |
|  | IV-1 | IV-2 | IV-3 | IV-4 | IV-1 | IV-2 |
| Conditions |  |  |  |  |  |  |
| Molar Ratio[1] |  | 1.94/0.97/1.0 |  |  |  |  |
| Temperature (° C.) |  | 90 |  |  |  |  |
| Time (hr) |  | 8 |  |  |  |  |
| Pressure (kPa) | 101.3 | 2.67 | 50 | 101.3 | 101.3 | 50 |
| Flow Rate of Nitrogen (mL/min) | 1300 | 140 | 1300 | 3000 | None | None |
| (m³/(h · kg)) | 0.11 | 0.012 | 0.11 | 0.26 |  |  |
| Evaluation | 6 | 6 | 12 |  |  | 6 |
| Phosphoric Monoester (% by weight) | 73.1 | 73.3 | 73.3 | 73.0 | 72.7 | 72.6 |
| Phosphoric Diester (% by weight) | 20.4 | 21.2 | 21.0 | 20.0 | 19.9 | 20.0 |
| Orthophosphoric Acid (% by weight) | 4.1 | 3.8 | 3.9 | 4.0 | 4.2 | 4.2 |
| Petroleum Ether-Soluble Component (% by weight) | 1.5 | 1.2 | 1.2 | 1.5 | 2.0 | 1.9 |
| Evaluation of Hue | 3 | 3 | 3 | 3 | 115 | 110 |
| Evaluation of Odor | 4 | 3 | 3.5 | 3.5 | 6 | 6 |

(Note)
Molar Ratio[1] Ethoxylate/$H_2O$/$P_2O_5$

From the results shown in Table 3, it can be seen that all of the phosphoric esters obtained in Examples IV-1 to IV-4 had excellent hue and reduced odor, as compared to those obtained in Comparative Examples IV-1 and IV-2.

EXAMPLE V

Preparation Example V-1

The amount 862.5 g (2.854 mol) of an ethylene oxide-added undecyl alcohol formed by adding 3 mol of ethylene oxide to 1 mol of undecyl alcohol (commercially available from Shell Oil Company under the trade name of Neodol 1-3) was mixed with 66.6 g of an 85% by weight aqueous phosphoric acid (the amount of phosphorus pentoxide being 0.288 mol and the amount of water being 1.422 mol). Thereto was gradually added 162.9 g (1.13 mol) of phosphorus pentoxide (effective content: 98.5% by weight), with maintaining the temperature of the mixture at 40° to 50° C. Thereafter, the temperature of the mixture was increased to 80° C., and the reaction was carried out for 12 hours. The value for the formula (1) was 3.0. Thereafter, 54.6 g of ion-exchanged water was added to the phosphoric ester to hydrolyze at 80° C. under normal pressure for 3 hours. The resulting phosphoric ester had a water content of 4.8% by weight, and an evaluation of odor of 6, showing strong odor, thereby making it impossible to use the phosphoric ester in a cleaning agent and the like.

Example V-1

Three-hundred grams of the phosphoric ester obtained in Preparation Example V-1 was hydrolyzed under reduced pressure by a batch process at 80° C. and under the pressure of 3 kPa for 3 hours. As a result, the phosphoric ester had a water content of 1.2% by weight. This resulting phosphoric ester was continuously supplied at a rate of 30 g/min. to the top of a packed tower [inner diameter: 50 mm, height: 22 cm, packing material: an article commercially available from SUMITOMO HEAVY METAL INDUSTRIES, LTD. under the trade name of Sulzer-Labopacking] of which pressure was controlled to 4 kPa, with increasing the temperature of the mixture to 130° C. To the bottom of the tower, steam was supplied at a rate of 15 g/min. at 90° C. to countercurrent-contact the phosphoric ester with the steam. After the contact time of 3 minutes passed, a deodorized product was obtained from the bottom of the tower. During this operation, foaming was little observed, so that the treating process could be carried out without any problems. The resulting phosphoric ester had an evaluation of odor of 2, which was excellent.

To 258.8 g of the phosphoric ester obtained as described above were added 7.0 g of ethanol and 21.0 g of dipropylene glycol to give a homogeneous solution, and thereafter 60.6 g of a 48% aqueous sodium hydroxide and 3.0 g of ion-exchanged water were added thereto with stirring, to give a transparent, homogeneous aqueous solution of a salt of the phosphoric ester in a high concentration. The resulting aqueous solution was composed of 67.9% by weight of the salt of the phosphoric ester, 2.0% by weight of ethanol and 6.0% by weight of dipropylene glycol, and had a viscosity of 870 mPa.s at 30° C. and a shearing rate of 50 $s^{-1}$.

Preparation Example V-2

The same procedures as in Preparation Example V-1 were carried out except that the reaction was carried out by using 968.3 g (4.516 mol) of myristyl alcohol in place of the ethylene oxide-added undecyl alcohol formed by adding 3 mol of ethylene oxide to 1 mol of undecyl alcohol used in Preparation Example V-1, 77.2 g of an 85% by weight aqueous phosphoric acid (the amount of phosphorus pentoxide being 0.336 mol and the amount of water being 1.644 mol) and 251.4 g (1.744 mol) of phosphorus pentoxide. The value for the formula (1) was 3.0. Thereafter, 25.9 g of ion-exchanged water was added to the phosphoric ester to hydrolyze at 80° C. under normal pressure for 3 hours. The resulting phosphoric ester had a water content of 1.8% by weight, and an evaluation of odor of 5, thereby making it impossible to use the phosphoric ester in a cleaning agent and the like.

Example V-2

The phosphorylation reaction was carried out by using the same apparatus as used in Example V-1. A part of the phosphoric ester obtained in Preparation Example V-2 was continuously supplied to the top of a packed tower [inner diameter: 50 mm, height: 22 cm, packing material: an article commercially available from SUMITOMO HEAVY METAL INDUSTRIES, LTD. under the trade name of Sulzer-Labopacking] of which pressure was controlled to 4 kPa, with increasing the temperature of the mixture to 130° C. at a rate of 30 g/min. To the bottom of the tower, nitrogen was supplied at a flow rate of 200 ml/min. under the standard state (0° C., 101.3 kPa), to countercurrent-contact the phosphoric ester with the nitrogen gas. After the contact time of 3 minutes passed, a deodorized product was obtained from the bottom of the tower. During this operation, foaming was little observed, so that the treating process could be carried out without any problems. The resulting phosphoric ester had an evaluation of odor of 2.5, which was excellent.

According to the present invention, since the odorous components contained in the phosphoric ester can be easily reduced, there is exhibited an excellent effect that a phosphoric ester having reduced odor can be easily and rapidly prepared.

What is claimed is:

1. A process for preparing a phosphoric ester having reduced odor, comprising contacting a phosphoric ester with at least one of an inert gas and steam at 100° to 160° C. in a packed tower.

2. The process according to claim 1, wherein the phosphoric ester is contacted with at least one of an inert gas and steam under a pressure of at most 20 kPa.

3. The process according to claim 1 or 2, wherein the phosphoric ester is contacted with steam.

4. A process for preparing a phosphoric ester having reduced odor, comprising repeating a set of processes comprising:
    (A) heating a phosphoric ester, and contacting the heated phosphoric ester with at least one of an inert gas and steam; and
    (B) cooling the phosphoric ester obtained in the step (A).

5. The process according to claim 4, wherein the temperature to which the phosphoric ester is heated and at which the phosphoric ester is contacted with at least one of an inert gas and steam is 100° to 160° C., and the cooling temperature of the phosphoric ester is at most 90° C.

6. The process according to claim 4 or 5, wherein the phosphoric ester is contacted with at least one of an inert gas and steam under a pressure of at most 20 kPa.

7. The process according to claim 4, wherein the phosphoric ester is contacted with steam.

8. The process according to claim 4, wherein the phosphoric ester is contacted with at least one of an inert gas and steam under the condition of water content of at most 3% by weight in the phosphoric ester.

9. A process for preparing a phosphoric ester having reduced odor, comprising adding water to a phosphoric ester, and distilling water from the phosphoric ester under reduced pressure.

10. The process according to claim 9, wherein the water content in the phosphoric ester during distillation of water is at most 10% by weight.

11. The process according to claim 9 or 10, wherein a set of processes comprising:
    (C) heating the phosphoric ester, adding water to the heated phosphoric ester, and distilling water from the phosphoric ester under reduced pressure; and
    (D) cooling the phosphoric ester obtained in the step (C) is repeated.

12. A process for preparing a phosphoric ester having reduced odor, comprising reacting an organic hydroxy compound with a phosphorylation agent, while introducing an inert gas into the mixture of the organic hydroxy compound and the phosphorylation agent.

13. The process according to claim 12, wherein the reaction is carried out under a reduced pressure of at most 70 kPa.

14. The process according to claim 12 or 13, wherein the inert gas is nitrogen gas.

* * * * *